United States Patent
Mioitti et al.

(10) Patent No.: US 6,535,577 B2
(45) Date of Patent: Mar. 18, 2003

(54) METHOD AND APPARATUS FOR RADIOGRAPHIC IMAGING HAVING AN ANTIDIFFUSION GRID

(75) Inventors: Luc Mioitti, Vanves (FR); Serge Muller, Guyancourt (FR); Andreas Rick, Plaisir (FR)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 0 days.

(21) Appl. No.: 09/948,355

(22) Filed: Sep. 7, 2001

(65) Prior Publication Data

US 2002/0122532 A1 Sep. 5, 2002

(30) Foreign Application Priority Data

Sep. 11, 2000 (FR) .............................. 00 11520

(51) Int. Cl.[7] .............................................. G21K 1/100
(52) U.S. Cl. ....................................... 378/155; 378/154
(58) Field of Search .................................. 378/154, 155

(56) References Cited

U.S. PATENT DOCUMENTS

| | | | | |
|---|---|---|---|---|
| 5,357,554 A | * | 10/1994 | Schneiderman et al. | .... 378/155 |
| 5,379,335 A | * | 1/1995 | Griesmer et al. | ............ 378/155 |
| 6,088,427 A | * | 7/2000 | Pagano | ......................... 378/155 |
| 6,181,773 B1 | * | 1/2001 | Lee et al. | ..................... 378/155 |
| 6,304,632 B1 | * | 10/2001 | Rick et al. | ................... 378/155 |

FOREIGN PATENT DOCUMENTS

| | | |
|---|---|---|
| EP | 0913838 | 5/1999 |
| FR | 2784569 | 4/2000 |

* cited by examiner

*Primary Examiner*—Robert H. Kim
*Assistant Examiner*—Allen C Ho
(74) *Attorney, Agent, or Firm*—Jay L. Chaskin

(57) ABSTRACT

Method and apparatus and computer programs and computer medium for improving quality of a radiographic image of an object obtained by an X-ray apparatus containing an antidiffusion grid, placed between the object and a receiver of radiographic images, The grid is displaced in rectilinear translation in its plane on pickup of the image, between two positions according to a time displacement law which is a continuous curve with a time precision of approximately ±10% presenting at least five separate parts, the displacement taking place at constant speed over at least two parts and at variable speed over at least one part.

19 Claims, 6 Drawing Sheets

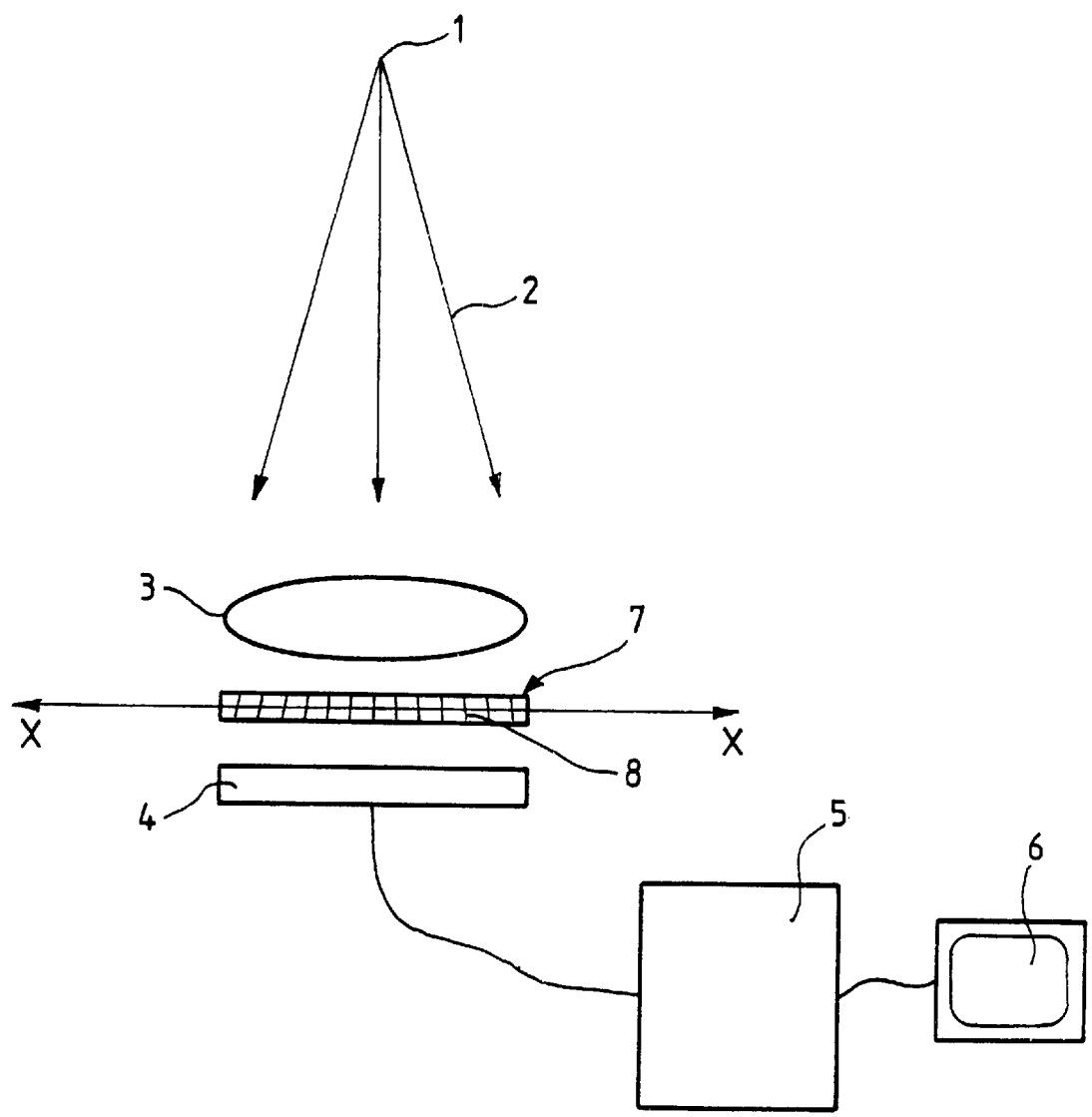
FIG_1

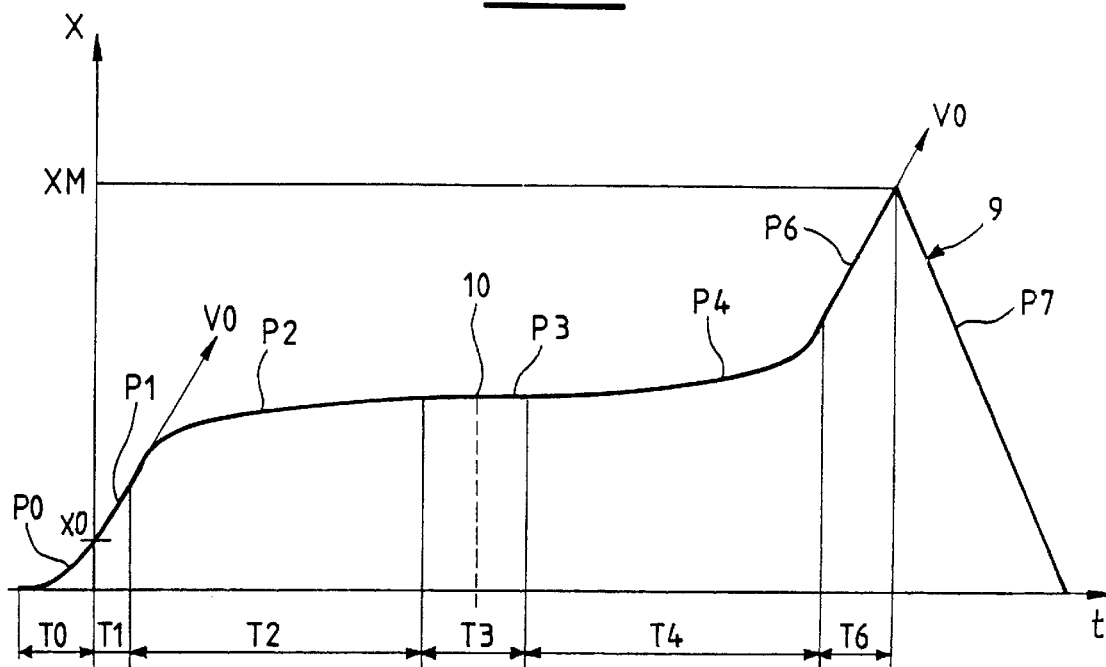
FIG_2
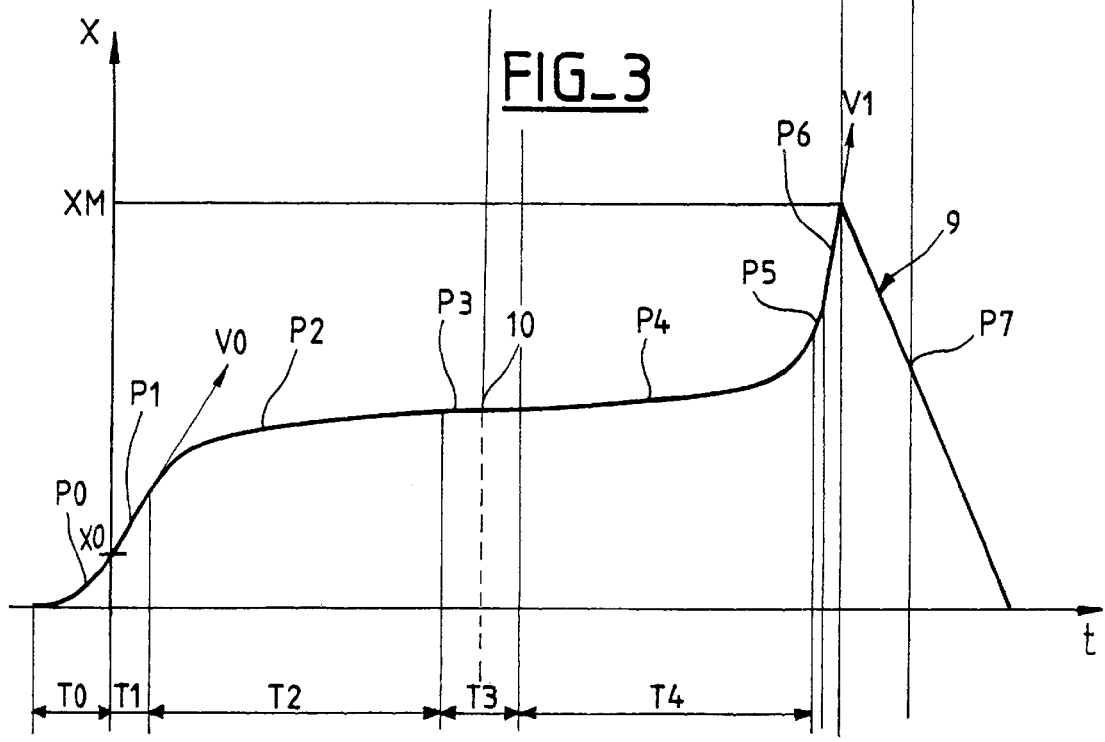
FIG_3

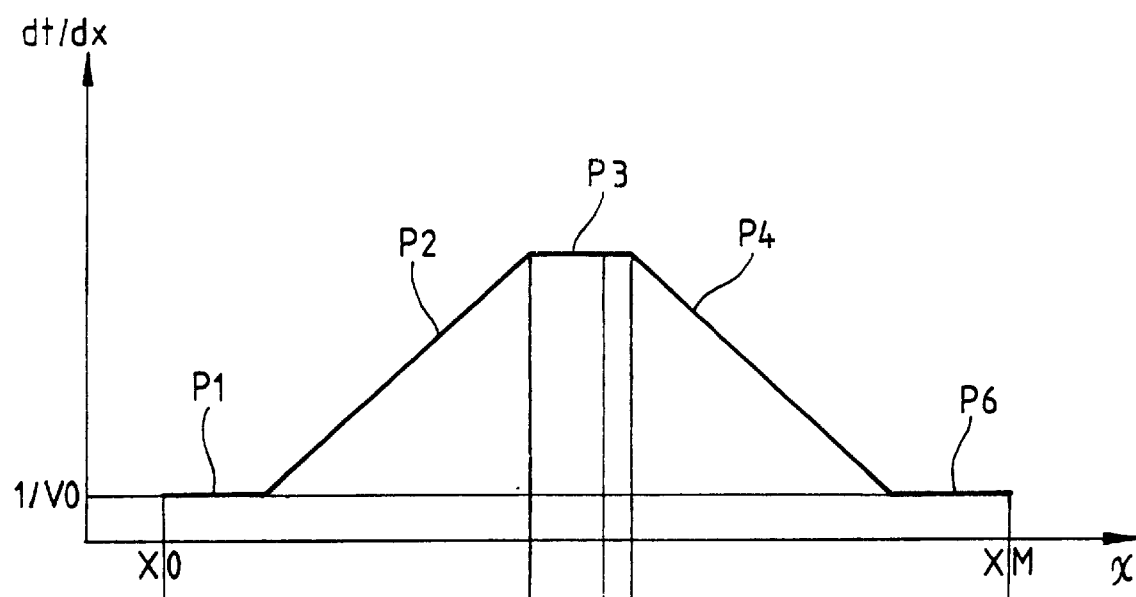
FIG_4
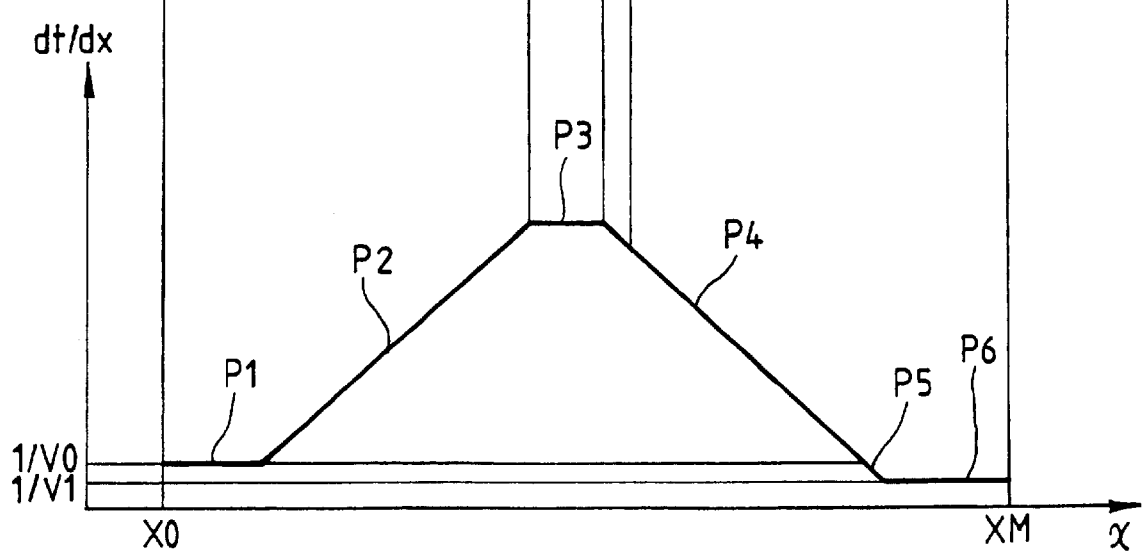
FIG_5

FIG_6
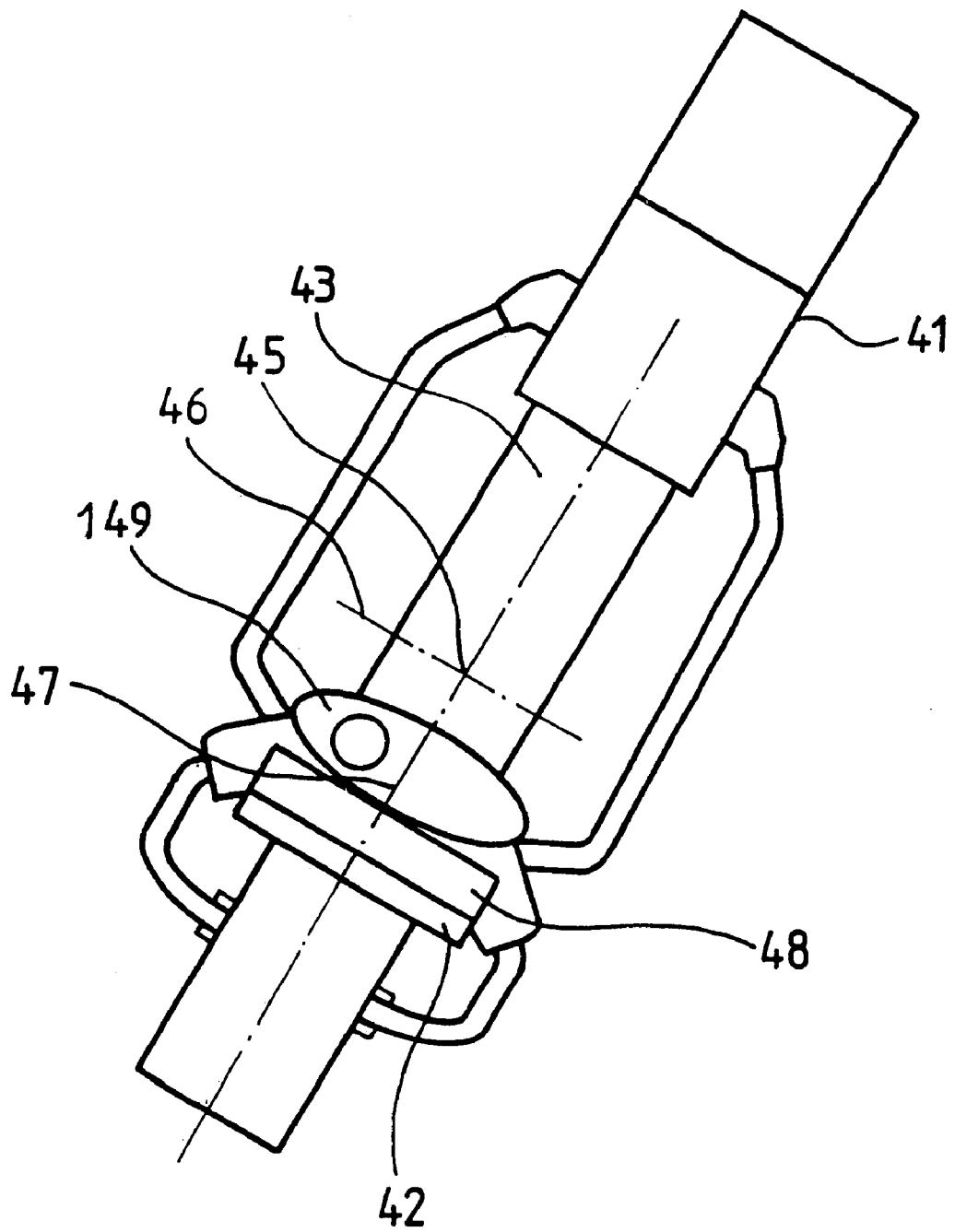

FIG_7
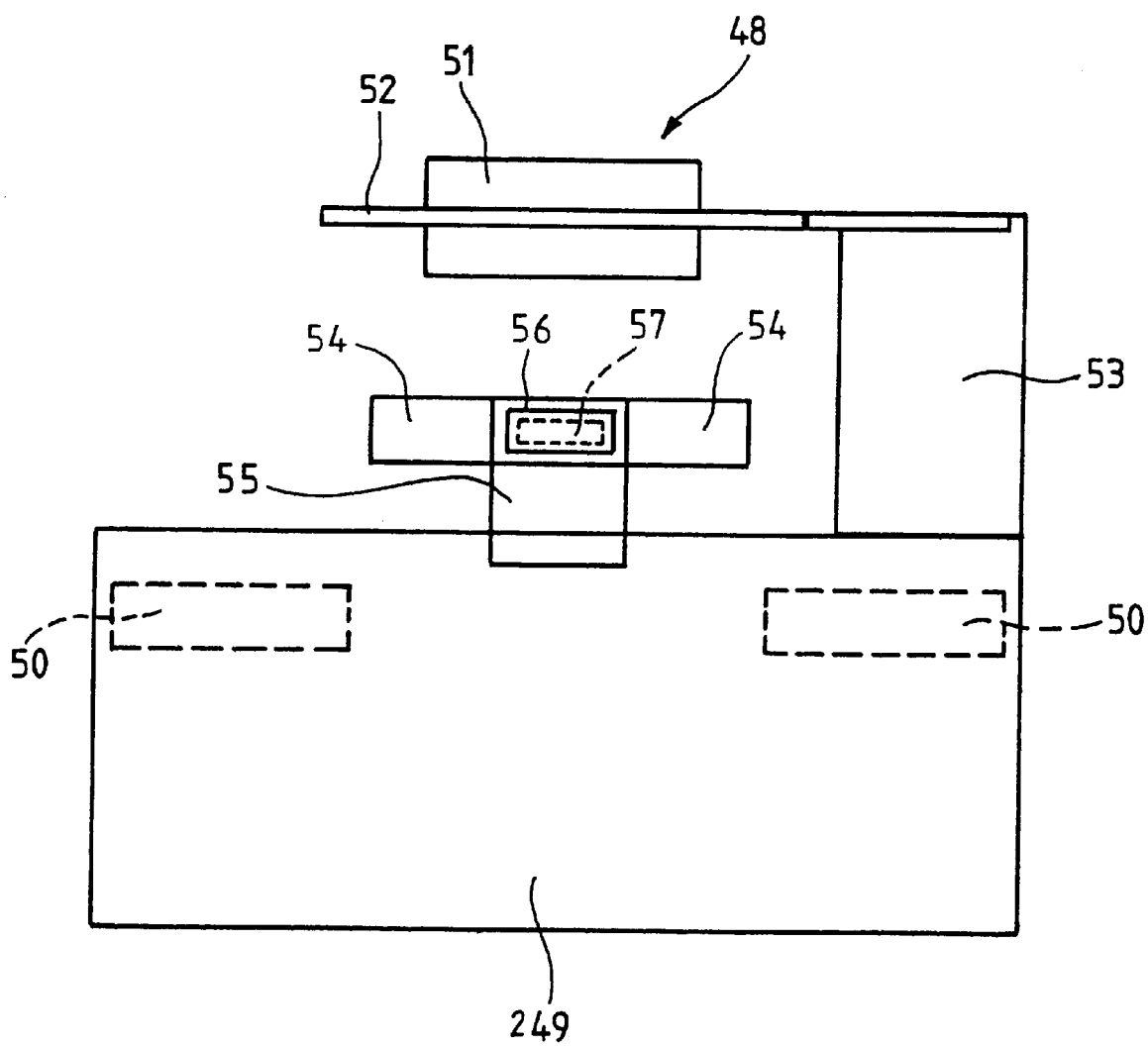

FIG_8
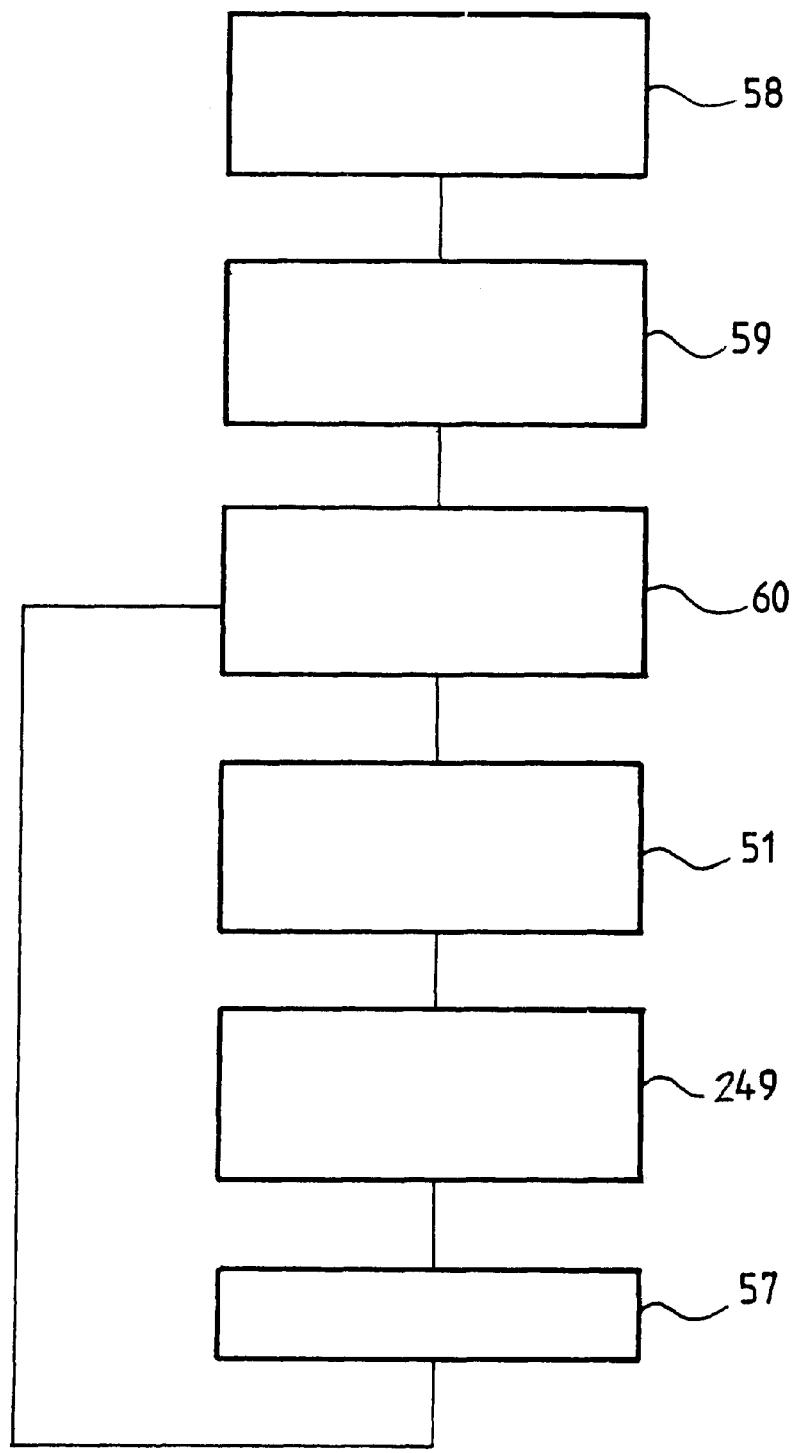

METHOD AND APPARATUS FOR RADIOGRAPHIC IMAGING HAVING AN ANTIDIFFUSION GRID

CROSS REFERENCE TO RELATED APPLICATIONS

This application claims the benefit of a priority under 35 USC 119 to French Patent Application No. 0011520 filed Sep. 11, 2000, the entire contents of which are incorporated by reference.

BACKGROUND OF THE INVENTION

The invention concerns the quality of a radiographic image of an object obtained by an X-ray apparatus having an antidiffusion grid. The invention is applicable advantageously but not exclusively to mammography examinations for the detection of microcalcifications inside a breast.

An X-ray apparatus, used notably in mammography, is equipped with an anti-diffusion grid placed between the object to be X-rayed, in this case a breast, and a receiver of radiographic images, for example, a CCD (charge-coupling) receiver. The antidiffusion grid is ordinarily composed of a series of strips which are all directed toward the focal point of radiation of X-rays emitted in the direction of the object and of the image receiver. Thus, the antidiffusion grids lets undiffused direct beams pass, while the diffused beams are absorbed by the strips. The resolution of the image receiver is generally finer than the space between two strips, which is typically in the order of 0.3 mm. As a result, the strips are visualized on the radiographic image obtained, which is particularly disturbing in mammography, for it renders the detection of microcalcifications more difficult.

One solution proposes displacing the grid during exposure, in rectilinear translation in its plane, that is, roughly perpendicular to the strips of the antidiffusion grid. The translation is carried out solely in one direction or alternately in both directions.

Another solution, as shown in FR-A-2,784,569, discloses a method of improvement of quality of an object obtained by an X-ray apparatus equipped with an antidiffusion grid with a law of displacement of the antidiffusion grid which is a continuous curve presenting a point symmetry relative to the point whose time coordinate is equal to half of the pickup time and whose spatial derivative of the time variable presents two symmetrical linear portions relative to the axis of symmetry passing through the middle of the range of displacement of the grid.

BRIEF DESCRIPTION OF THE INVENTION

The invention is directed to substantially elimination of the visible traces of strips of the antidiffusion grid on the X-ray film.

The invention is also directed to obtaining an improvement of image quality with a mechanically simple solution for displacement of the antidiffusion grid.

The invention is directed to a particular profile of displacement of the antidiffusion grid.

The invention is also directed to an improvement of image quality realizing that at a beginning of exposure, the exposure time is known with a rather wide margin of imprecision, for example, on the order of 10%.

The invention is a method of improvement of quality of a radiographic image of an object obtained by an X-ray apparatus containing an antidiffuision grid, placed between the object and a receiver of radiographic images, a grid that is displaced in rectilinear translation in its plane on pickup of the image, between a starting position and an arrival position and according to a time displacement law with a time precision of approximately ±10%. The displacement law is a continuous curve presenting at least five separate parts, the displacement taking place at constant speed over at least two parts and at variable speed over at least one other part.

An embodiment of the invention also concerns a computer program comprising program code means for using the stages of the method, when the program is operating on a computer.

An embodiment of the invention also concerns a support capable of being read by a reading device of program code means which are stored there and fit for use of the stages of the method, when the program is operating on a computer.

An embodiment of the invention also concerns a radiological imaging device comprising an X-ray beam emitter, a receiver of the X-ray beam after it has crossed an organ to be studied, a moving antidiffusion grid and an arithmetical unit able to control the emitter, to control displacement of the antidiffusion grid and to process data coming from the receiver.

BRIEF DESCRIPTION OF THE DRAWINGS

An embodiment is illustrated by the following drawings:

FIG. 1 is a schematic view of an exemplary X-ray apparatus in which an embodiment of the method can be performed;

FIGS. 2 and 3 illustrate two embodiments of the application of a law of displacement of a grid;

FIGS. 4 and 5 illustrate an embodiment of the spatial derivative of the time variable of the law of displacement of FIGS. 2 and 3, respectively;

FIG. 6 is a view in perspective of an embodiment of a radiology apparatus which can be used to perform the method;

FIG. 7 is a schematic view of a grid mounted in a filter element; and

FIG. 8 is a flow sheet of an embodiment of an X-ray device.

DETAILED DESCRIPTION OF THE INVENTION

According to an embodiment of the invention the parts can be calculated before imaging by taking the imprecision into account. The parts can be recalculated during imaging if the imprecision diminishes. The imprecision can even become nil.

According to an embodiment of the invention, the duration of at least a part at constant speed is readjusted in a position between the starting position and the arrival position, exclusive of limits.

According to an embodiment of the invention, the displacement is carried out at high constant speed over a first part. The duration of the first part depends on the precision of synchronization of the start of imaging with the start of displacement.

According to an embodiment of the invention, the displacement is carried out at decreasing speed over a second part.

According to an embodiment of the invention of the invention, the displacement is carried out at low constant speed over a third part. The duration of the third part depends on the imprecision of a prediction of duration of imaging. If at the end of the second part, the imprecision diminishes, the duration of the third part is reduced in accordance with the diminution of the imprecision.

According to an embodiment of the invention, the displacement is carried out at constant speed on a fourth part. The modulus of acceleration may be equal to that of the second part. The duration of the fourth part may be equal to that of the second part.

According to an embodiment of the invention, displacement is carried out at increasing speed on a fifth part. The fifth part can form an extension of the fourth part in time.

According to an embodiment of the invention, displacement is carried out at constant speed and increased on a sixth part. The duration of the sixth part may be equal to the imprecision.

According to an embodiment of the invention, the increased rate of displacement ranges between approximately three times and approximately ten times the value of the ratio between the range of displacement and the pickup time. In other words, that increased rate of displacement ranges between approximately three times and approximately ten times the value of a linear rate of displacement of the grid between the starting position and the pickup position.

In an embodiment of the invention, the second and fourth parts present a profile of evolution of the "position" variable, function of the square root of the "time" variable.

In an embodiment of the invention arithmetical unit comprises a means for displacing the antidiffusion grid in rectilinear translation in its plane on the pickup of the image, between a starting position and an arrival position and according to a time displacement law. The displacement law is a continuous curve with a time precision of approximately ±10%, presenting at least five separate parts, displacement being carried out at constant speed over at least two parts and at variable speed over at least one part.

A better time precision of approximately ±8%, and even ±5%, could be envisaged.

The displacement law comprises a deceleration part and an acceleration part that are not symmetrical. At the beginning, in the middle and at the end of X-ray exposure, line segments in the course of which the grid is displaced at constant speed are provided to take into account a number of imprecisions or imperfections.

A part of the translation situated at the start of movement and carried out at constant speed makes it possible to minimize the variations of image quality with the unpredictable variations of synchronization between the start of translation and the start of imaging and to improve the worst statistical case in terms of image quality.

The part of the translation situated in the middle and carried out at constant speed makes it possible to maximize the time during which translation is carried out at low speed. That speed remain high enough to avoid swinging between dynamic frictions and static frictions and makes it possible to satisfy the requirements of continuity with other parts being carried out according to laws making it possible to enhance image quality in relation to a law of displacement taking place wholly at constant speed.

The law of displacement makes it possible to adjust dynamically during pickup the duration of different parts of the curve as a function of diminution of the imprecision of prediction of pickup time. The dynamic readjustment is made by diminishing the duration of the final linear part in order to match it to the prediction imprecision, by shortening the central linear part, by extending the part situated between those two and by increasing the speed of the final linear part, so as to obtain a continuity of speed among the three parts mentioned and a maximum displacement in the course of pickup.

Before the start of the movement, the maximum pickup time is sought, taking the prediction imprecision into account. The parts of the curve are calculated to have a maximum displacement at the end of the maximum time. The duration of the fifth part is then planned to be nil. The speed, on the first part and sixth part, is identical. During pickup and preferably before the start of the third part, the imprecision of prediction is recalculated. The time range of the sixth part is then reduced to match the new prediction imprecision. The time range of the fifth part is increased in order to obtain a maximum displacement and speed on the latest date of completion of pickup according to the new prediction. The duration of the third part of the curve is modified in order to take into account the change of latest date of completion of pickup according to the new prediction, the reduction of duration of the sixth part and the increased duration of the fourth part.

The final speed is markedly greater than it was previously, even though there is no significant reduction of prediction imprecision during imaging. Another advantage which proves important when the reduction is consequential consists of the fact that the distance covered by the grid during pick-up is markedly greater.

In FIG. 1, reference 1 designates the focal point of an X-ray tube emitting an X-ray beam 2 in the direction of an object to be X-rayed 3. The radiographic images are received on a receiver 4, comprising, for example, a matrix sensor of solid state or CCD type with a scintillator. The receiver 4 is connected to processing means 5 architectured around a microprocessor and the X-rayed images can be visualized on a display screen 6. Between the object 3 to be X-rayed and the receiver 4, an antidiffusion grid 7 is placed, moving in translation roughly perpendicular to the radiation emitted, that is, in direction XX of FIG. 1. The grid 7 is made up of a plurality of strips 8, all directed toward the focal point 1. The strips 8, typically spaced in the order of 0.3 mm, make it possible to absorb the radiations diffused by the object and let only the direct radiation pass.

The processing means 5 comprise, in addition, at least one memory and at least one control program stored in memory and capable of being executed by the microprocessor.

In order to avoid visualization of the strips 8 on the images obtained, the grid 7 is displaced in rectilinear translation in its plane, that is, in direction XX, along a predetermined profile, on pickup of each image, between a starting position and an arrival position.

The distance separating the edge of one strip from the edge of the immediately adjacent strip being designated as "period" of the grid, that is, a distance equal to the thickness of the strip plus the distance between two adjacent strips 8, it was observed that one of the main reasons producing visualization of the strips 8 on the images was the fact that the number of grid periods passing between the X-radiation and each pixel of the image receiver was not a whole number. In other words, the part of a period of the grid not passing between the radiation 2 and a pixel of the image receiver renders the corresponding strip of the grid visible on the image obtained.

Furthermore, it was observed that the fact that the grid 7 was displaced at an increased rate of displacement in proximity to the starting position and arrival position made it possible to reduce visualization of traces of the grid on the X-rayed image, for this contributed to a reduction of exposure time of incomplete periods of the grid situated at the ends of same.

However, it is not necessary to provide an increased rate of displacement in the middle of the displacement range, since, in that zone, complete grid periods pass between the X-radiation and a given pixel of the image receiver.

In other words, by reason of the periodicity of the grid, the intensity of the X-radiation arriving on the image receiver is the time integral on the period of exposure of the incident energy multiplied by the attenuation coefficient. This is the time integral which makes it possible to render the incomplete periods of the grid visible on the image and to eliminate the traces of the strips corresponding to complete periods of the grid being displaced between the radiation 2 and the pixels of the sensor 4.

In general, the displacement profile of the grid 7 between the starting position X0 and the arrival position XM during the exposure time TP of each image (TP=T1 to T6) is a continuous curve illustrated in FIGS. 2 to 5 and comprising six parts P1 to P6:

P1: The displacement takes place at roughly constant high speed. Its duration is a function of the precision of synchronization of the start of imaging with the start of displacement;

P2: The displacement takes place at decreasing speed;

P3: The displacement take place at low constant speed. Its duration is a function of the imprecision of a prediction of imaging time. If at the end of the second part, the imprecision diminishes, the duration of the third part is adjusted to the diminution of the imprecision;

P4: The displacement takes place at increasing speed. The absolute value of acceleration may be equal to that of the second part. The duration of the fourth part may be equal to that of the second part;

P5: The displacement takes place at increasing speed. The fifth part can form an extension of the fourth part in time, which signifies a conservation of acceleration;

P6: The displacement takes place at high constant speed. The duration of the sixth part may be equal to the imprecision.

The rate of displacement V0 in proximity to the starting position and the arrival position must be high, for example, ranging between approximately three times and approximately ten times the value of the ratio (XM-X0/TP) between the range of displacement and the pick-up time, that is, three to ten times higher than the value of a linear rate of displacement.

Parts P2 and P4 are symmetrical relative to point 10 of time coordinate T1+T2+T3/2. Each of those portions P2 and P4 represents a profile of evolution of the "position" variable (X), which is a function of the square root of the "time" variable (t).

More precisely, the equation of portion P2 is given by formula (1) below:

$$X(t) = Ao + b\sqrt{ct - TC0} \quad \text{for } t \leq T1 + T2 + T3/2 \quad (1)$$

while the equation of portion P4 is given by formula (2) below:

$$X(t) = A1 - b\sqrt{ct + TC1} \quad \text{for } t \geq T1 + T2 + T3/2 \quad (2)$$

In those formulas, Ao, A1, b, c, TC0 and TC1 are constants making it possible to adjust the position of the grid 7 to value X0 for time T0 and to value XM for time T6 and making it possible to join both portions P2 and P4 to point 10.

In order to obtain the high speed V0 at pickup starting time T0, a preliminary displacement of the grid 7 is provided for between origin and position X0 along a displacement curve P0 having a parabolic shape. Furthermore, after pickup completion time T6, that is, when the grid 7 has reached position XM, the latter returns to zero position through a linear decline 9 (terminal portion P7).

In FIGS. 2 and 4, it can be seen that part P5 is absent; in other words, its duration is nil. The displacement is determined before the start of pickup and refined after a diminution of the imprecision acquired before part P3.

The value of imprecision on the imaging time prediction, as it is known before the start of displacement, is noted $\pm\Delta 0$. The value of imprecision on the imaging time prediction, as it is subsequently known, that is, during displacement, is noted $\pm\Delta 1$.

The spatial derivative of the time variable of the curve illustrated in FIG. 2 is represented in FIG. 4. The spatial derivative of the time variable of the curve illustrated in FIG. 3 is represented in FIG. 5.

Such a curve profile makes it possible to reduce the visibility of the strips of the grid 7 on the images obtained and, therefore, to improve their quality in order to facilitate, notably, the detection of microcalcifications, regardless of the exposure time. Furthermore, the invention is avoids of any alternating movement, which renders it less sensitive to mechanical parameters.

The resulting improvement of image quality does not necessitate any modification of the image processing and acquisition software.

In addition, the displacement of the grid 7 is generally obtained from a step or other type motor, driven by a control unit, equipped with a processor, memories, communication bus and control program stored in a memory and capable of generating an instruction signal when executed by the processor. The instruction signal is delivered to the motor with generally a time and a period of not negligible value.

The motor by nature generates mechanical oscillations on displacement. When the frequency of the oscillations corresponds to the frequency of spacing of the strips 8 of the grid 7, scanning peaks are then obtained which are translated by an increased visibility of the strips 8 on the images. It was observed that the profile of displacement according to the invention minimized that undesirable effect.

Finally, although there is a marked improvement of image quality with a spatial derivative profile dt/dx comprising of not necessarily linear portions, the visibility of the strips is even more reduced if the spatial derivative dt/dx presents such linear portions.

As can be seen in FIG. 6, a radiology device comprises an X-ray source 41 and a digital receiver 42 supported by an arm 43 which can swing in relation to the vertical plane of symmetry of the radiology device, and a control and processing means not represented. The arm 43 is provided on its front face with a plurality of holes in order to be able to attach a puncture system or a breast plate of adjustable height.

The swing axis passes through the isocenter 45 defined by the intersection of an axis 47 of propagation of X-rays and an axis 46 parallel to the plane of the receiver 42.

The radiology device further contains a filter element 48, also called "bucky," placed between the organ X-rayed 149 and the digital receiver 42. The filter element 48 comprises a grid, such as the grid 7 of FIG. 1.

The control and processing means comprises electronic means, not represented, connected to the receiver 42, to the filter element 48 and to the source 41 by electric cables. The control and processing means can include a screen for display of the images of the organ X-rayed and a keyboard. The control and processing means can be equipped with software intended for calculation of three-dimensional coordinates of points of the organ X-rayed from two images taken at different angles thanks to pivoting of the arm 43. An excellent visualization can then be obtained of particular zones of the organ X-rayed upon a diagnosis, as well as of the positioning of the needle in the organ X-rayed upon a biopsy, using optimized display methods.

In operation, the X-rays are emitted by the source 41, cross the organ X-rayed 149 and the filter element 48 and reach the receiver 42.

In other embodiments, an X-ray receiver is placed on the path of the X-ray beam in a given position relative to the X-ray emitter and includes a scintillator and a matrix camera or a solid state detector, etc.

As can be seen in FIG. 7, a filter element 48 comprises a grid 249 provided with skids 50 made of a material with low coefficient of friction in order to make possible an easy displacement of the grid 249, a linear motor 51 with magnetic core 52 connected to the grid 249 by a brace 53, two other skids 54 connected to the grid 249 by a support 55, and a magnet 56 placed between the skids 54. The linear motor 51 is capable of displacing the grid 249 in translation and is controlled by the control and processing means. The magnet 56 forms a coder whose magnetic field can be detected by one or more magnetic field sensors 57, for example, with Hall effect, fastened to a frame, not represented, of the filter element 48, the frame being designed to be integral with a radiology device and to support a stationary part of the linear motor 51. The sensors 57 are able to emit information on position of the grid 249 with a degree of precision to the control and processing means.

As can be seen in FIG. 8, the control and processing means includes a module 58 for estimate of exposure time and a module 59 for calculation of a law of optimal displacement receiving an estimate of exposure time from module 58. The law of optimal displacement constitutes an instruction of position of the grid as a function of time, which is sent to a filter element control unit 60. The control unit 60 sends a current (or voltage) feeding the linear motor 51 of the filter element and receives the information on position of the grid 249 emitted by the position sensor or sensors 57.

Various modifications in structure and/or steps and/or function may be made by one skilled in the art without departing from the scope of the invention.

What is claimed is:

1. A method of radiographic imaging of an object by an apparatus having an antidiffusion grid, placed between the object and a receiver of radiographic images, wherein the grid is displaced in rectilinear translation in its plane between a starting position and an arrival position comprising the step of translating the grid according to a time displacement law, in which the displacement law is a continuous curve with a time precision of approximately ±10% presenting at least five separate parts, the displacement taking place at constant speed over at least two parts and at variable speed over at least one part.

2. The method according to claim 1 in which the duration of at least one part at constant speed is readjusted in a position between the starting position and the arrival position, exclusive of limits.

3. The method according to claim 1 in which the displacement take place at high constant speed over one part and at decreasing speed over a second part.

4. The method according to claim 2 in which the displacement take place at high constant speed over one part and at decreasing speed over a second part.

5. The method according to claim 1 in which the displacement takes place at low constant speed over a third part.

6. The method according to claim 2 in which the displacement takes place at low constant speed over a third part.

7. The method according to claim 3 in which the displacement takes place at low constant speed over a third part.

8. The method according to claim 5 in which the duration of the third part is a decreasing function of imprecision of an imaging time prediction.

9. The method according to claim 6 in which the duration of the third part is a decreasing function of imprecision of an imaging time prediction.

10. The method according to claim 7 in which the duration of the third part is a decreasing function of imprecision of an imaging time prediction.

11. The method according to claim 1 in which the displacement takes place at increasing speed over a fourth part.

12. The method according to claim 11 which the modulus of acceleration is equal to that of the second part.

13. The method according to claim 1 in which the displacement takes place at increasing speed over a fifth part.

14. The method according to claim 1 in which the displacement takes place at high constant speed over a sixth part.

15. Method according to claim 14 in which the duration of the sixth part is equal to the imprecision.

16. Computer program containing program code means for applying the stages of the method according to claim 1 when the program is processed on a computer.

17. Support capable of being read by a device for reading program code which are stored therein and are suitable for application of the stages of the method according to claim 1.

18. Radiological imaging apparatus comprising:

radiation beam emitter;

a receiver of the beam after it has crossed an organ to be studied;

a movable grid; and an arithmetical unit able to control the emitter, to control displacement of the grid and to process data coming from the receiver, the arithmetical unit comprising a means for displacing the grid in rectilinear translation in its plane between a starting position and an arrival position and according to a time displacement law, the displacement law being a continuous curve with a time precision of approximately ±10%, presenting at least five separate parts, displacement being carried out at constant speed over at least two parts and at variable speed over at least one part.

19. The method according to claim 18 in which the duration of at least one part at constant speed is readjusted in a position between the starting position and the arrival position, exclusive of limits.

* * * * *

UNITED STATES PATENT AND TRADEMARK OFFICE
CERTIFICATE OF CORRECTION

PATENT NO.        : 6,535,577 B2                          Page 1 of 1
APPLICATION NO. : 09/948355
DATED             : March 18, 2003
INVENTOR(S)       : Miotti et al.

It is certified that error appears in the above-identified patent and that said Letters Patent is hereby corrected as shown below:

TITLE PAGE
(12) United States Patent:
    Delete "Mioitti et al." and insert therefor -- Miotti et al --

(75) Inventors:
    After "Luc" delete "Mioitti" and insert therefor -- Miotti --

Signed and Sealed this

Second Day of October, 2007

JON W. DUDAS
*Director of the United States Patent and Trademark Office*